United States Patent
Wang et al.

(10) Patent No.: US 11,517,246 B2
(45) Date of Patent: Dec. 6, 2022

(54) METHOD FOR DIAGNOSING NEUROLOGICAL DISORDER BY MAGNETIC RESONANCE IMAGING

(71) Applicants: Chang Gung University, Taoyuan (TW); Chang Gung Memorial Hospital, Linkou, Taoyuan (TW); Chang Gung Medical Foundation Chang Gung Memorial Hospital at Keelung, Keelung (TW)

(72) Inventors: Jiun-Jie Wang, Taoyuan County (TW); Yi-Hsin Weng, Taoyuan (TW); Shu-Hang Ng, Taoyuan (TW); Jur-Shan Cheng, Taoyuan (TW); Yi-Ming Wu, Taoyuan (TW); Yao-Liang Chen, Taoyuan (TW); Wey-Yil Lin, Taoyuan (TW); Chin-Song Lu, Taoyuan (TW); Wen-Chuin Hsu, Taoyuan (TW); Chia-Ling Chen, Taoyuan (TW); Yi-Chun Chen, Taoyuan (TW); Sung-Han Lin, Taoyuan (TW); Chih-Chien Tsai, Taoyuan (TW)

(73) Assignees: Chang Gung Memorial Hospital, Linkou, Taoyuan (TW); Chang GungUniversitv, Taoyuan (TW); Change Gung Medical Foundation Chang Gung Memorial Hospital at Keelung, Keelung (TW)

( * ) Notice: Subject to any disclaimer, the term of this patent is extended or adjusted under 35 U.S.C. 154(b) by 640 days.

(21) Appl. No.: 15/923,919

(22) Filed: Mar. 16, 2018

(65) Prior Publication Data
US 2018/0263548 A1    Sep. 20, 2018

(30) Foreign Application Priority Data
Mar. 17, 2017  (TW) .................................. 106108922

(51) Int. Cl.
A61B 5/00     (2006.01)
A61B 5/055    (2006.01)
G06T 7/00     (2017.01)

(52) U.S. Cl.
CPC .......... *A61B 5/4064* (2013.01); *A61B 5/0042* (2013.01); *A61B 5/055* (2013.01);
(Continued)

(58) Field of Classification Search
CPC ..... A61B 5/4064; A61B 5/0042; A61B 5/055; A61B 5/4088; A61B 5/4082;
(Continued)

(56) References Cited

U.S. PATENT DOCUMENTS

2010/0183202 A1* 7/2010 Takahashi ............. A61B 6/037
                                                           382/128
2013/0102877 A1* 4/2013 Mori .................. G01R 33/5608
                                                           600/410

(Continued)

*Primary Examiner* — Serkan Akar
*Assistant Examiner* — Amal Aly Farag
(74) *Attorney, Agent, or Firm* — Schwegman Lundberg & Woessner, P.A.

(57) ABSTRACT

Disclosed herein is a method for diagnosing a neurological disorder based on at least one magnetic resonance imaging (MRI) image. The method includes identifying brain image regions that contain a respective portion of diffusion index values of at least one diffusion index. For each of the brain image regions, a characteristic parameter based on the respective portion of the diffusion index values is calculated. a diagnoses is then made for the brain using one of predetermined categories of the neurological disorder by performing classification on a combination of the characteristic parameters via a classifier.

9 Claims, 16 Drawing Sheets

(52) U.S. Cl.
CPC .......... *A61B 5/4082* (2013.01); *A61B 5/4088* (2013.01); *G06T 7/0012* (2013.01); *A61B 5/7264* (2013.01); *G06T 2207/10088* (2013.01); *G06T 2207/10092* (2013.01); *G06T 2207/20081* (2013.01); *G06T 2207/30016* (2013.01)

(58) Field of Classification Search
CPC ................ A61B 5/7264; G06T 7/0012; G06T 2207/20081; G06T 2207/10092; G06T 2207/10088; G06T 2207/30016
See application file for complete search history.

(56) References Cited

U.S. PATENT DOCUMENTS

| | | | | |
|---|---|---|---|---|
| 2013/0279771 | A1* | 10/2013 | Wang | G06T 7/0012 382/128 |
| 2014/0155730 | A1* | 6/2014 | Bansal | A61B 5/245 600/409 |
| 2016/0154010 | A1* | 6/2016 | O'Bryant | A61B 5/4088 506/9 |
| 2018/0204327 | A1* | 7/2018 | Matthews | G06K 9/00147 |

* cited by examiner

METHOD FOR DIAGNOSING NEUROLOGICAL DISORDER BY MAGNETIC RESONANCE IMAGING

CROSS-REFERENCE TO RELATED APPLICATION

This application claims priority of Taiwanese Patent Application No. 106108922, filed on Mar. 17, 2017, which is hereby incorporated by reference herein in its entirety.

FIELD

The disclosure relates to a method for diagnosing a neurological disorder, and more particularly to a method for diagnosing a neurological disorder by magnetic resonance imaging (MRI).

BACKGROUND

For the sake of minimizing the body burden of a radioactive tracer in an examinee, and for the sake of achieving relatively high spatial resolution and contrast in imaging, the magnetic resonance imaging (MRI) technique has been widely used, but mostly for the ruling out of concomitant neurological disorder. A conventional approach of diagnosing a neurological disorder by diffusion MRI usually includes a step of selecting manually a volume of interest (VOI) in an MRI brain image of the examinee or a step of performing voxel-wise analysis on the MRI brain image.

However, manual selection of a VOI in an MRI brain image requires a higher level of expertise and might sometimes lead to misjudgment due to practitioner's personal subjectivity. Voxel-wise analysis does not parcel the MRI brain image based on structural features of a brain, so regional characteristics of the brain might be neglected. In addition, an excessive amount of voxels generated by voxel-wise analysis might increase difficulty of statistical explanation.

SUMMARY

Therefore, an object of the disclosure is to provide a method that is adapted for diagnosing a neurological disorder based on at least one magnetic resonance imaging (MRI) image which is associated with a brain examined and that can alleviate at least one of the drawbacks of the prior art.

According to the disclosure, the method is to be implemented by a computing device. The method includes steps of:

a) identifying, according to said at least one MRI image, a plurality of brain image regions each of which contains a respective portion of diffusion index values of at least one diffusion index, which results from image processing performed on said at least one MRI image;

b) for each of the brain image regions, calculating at least one characteristic parameter based on the respective portion of the diffusion index values of said at least one diffusion index; and c) diagnosing the brain examined with one of predetermined categories of the neurological disorder by performing classification on a combination of the characteristic parameters of the brain image regions via a classifier associated with the predetermined categories of the neurological disorder.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1A:
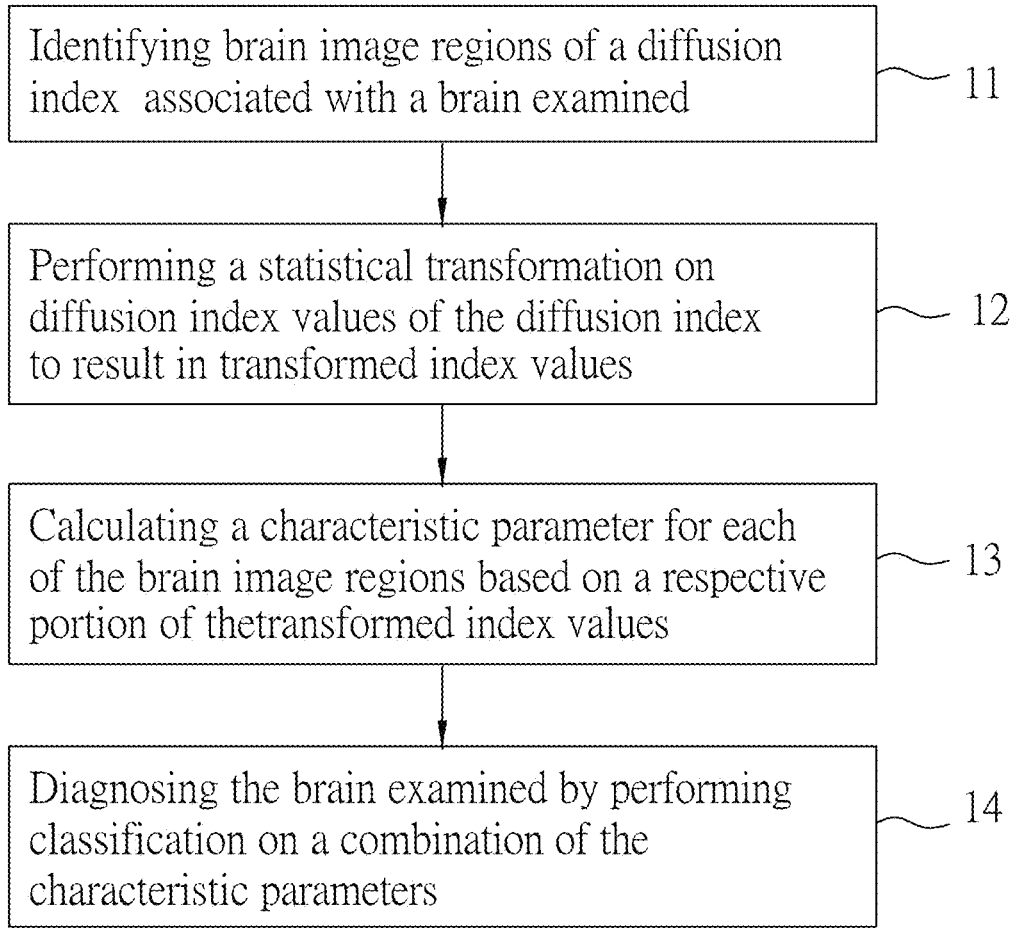
FIGS. 1A and 1B cooperate to illustrate a flow diagram of an embodiment of a method for diagnosing a neurological disorder by magnetic resonance imaging (MRI) according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1B:
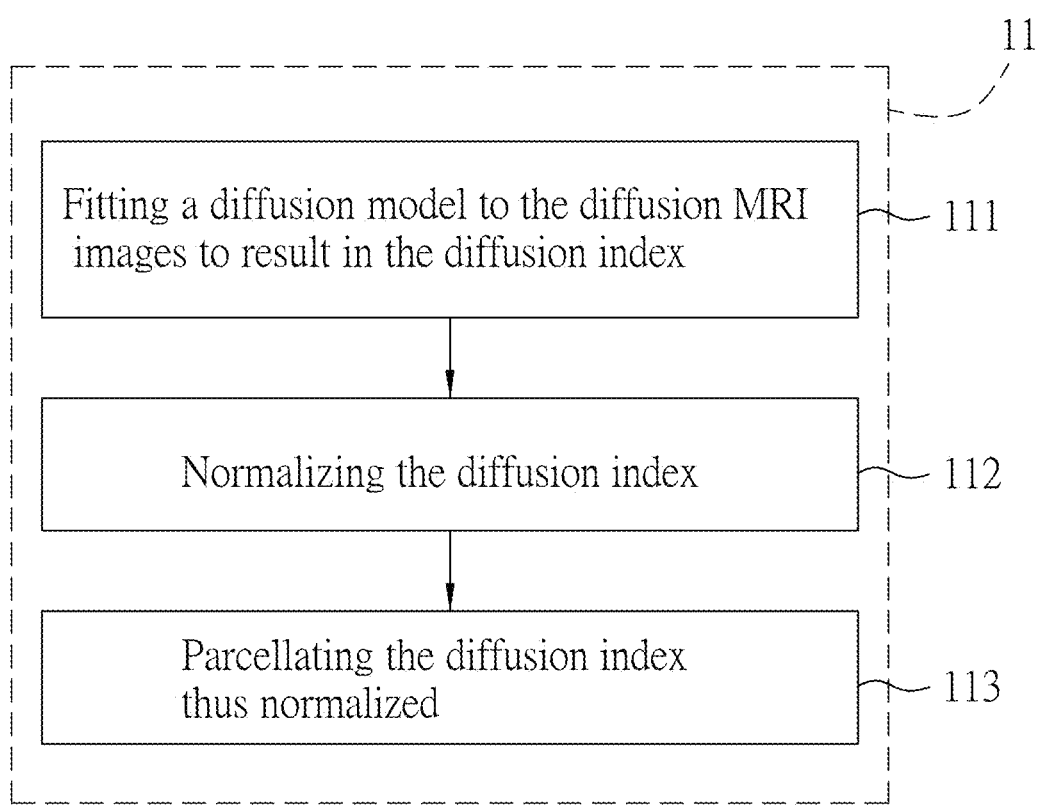
Figure 2:
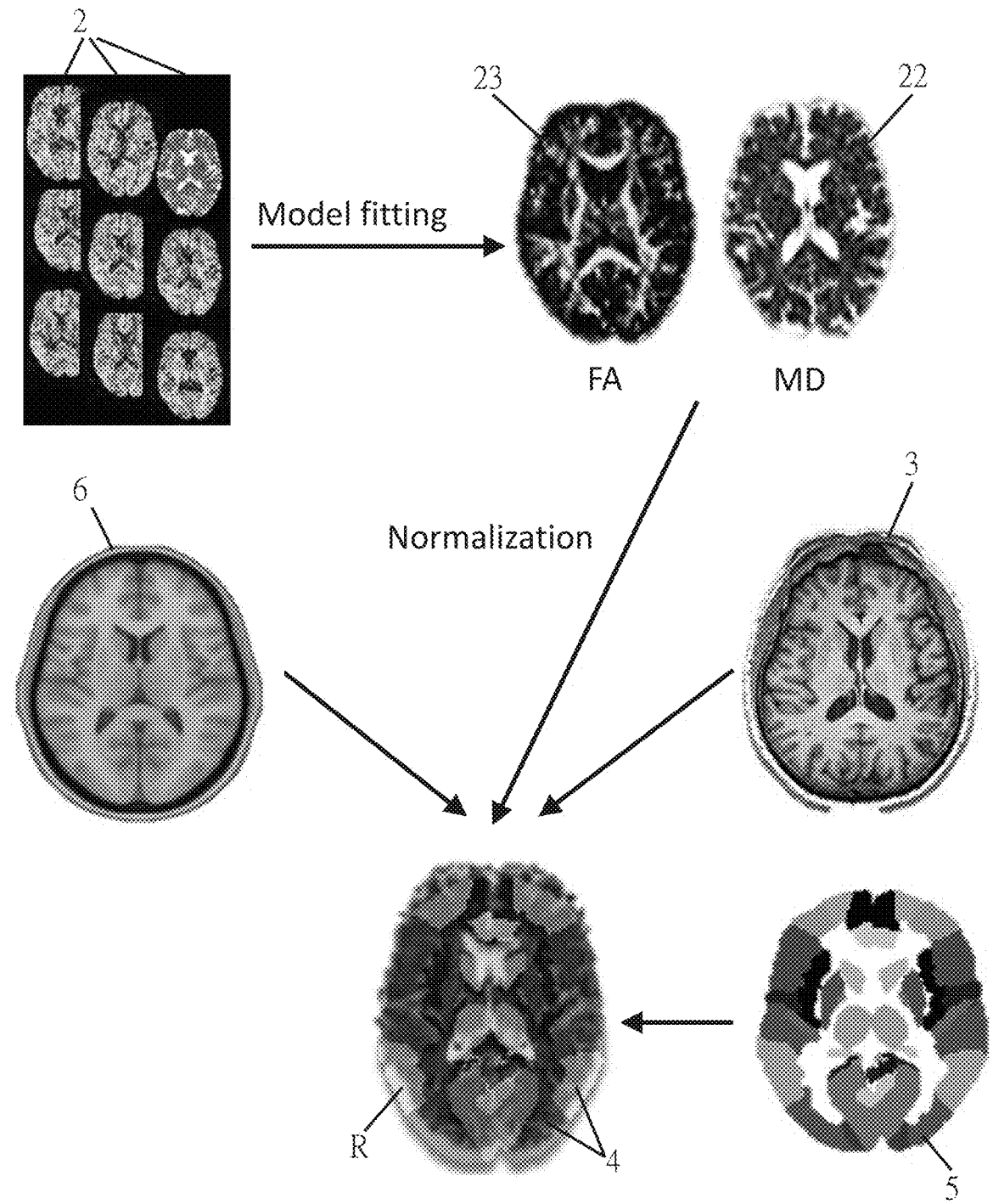
FIG. 2 is a schematic diagram illustrating an embodiment of a step of identifying a plurality of brain image regions based on a plurality of diffusion MRI images and an anatomical image in the method of this disclosure.

Referring to FIGS. 1A, 1B and 2, an embodiment of a method for diagnosing a neurological disorder based on at least one magnetic resonance imaging (MRI) image according to this disclosure is illustrated. The MRI image is associated with a brain examined, and is exemplified by a diffusion weighted image (DWI). In the method of this embodiment, diagnosis of the neurological disorder is made based on a plurality of diffusion MRI images 2 (for example, nine diffusion MRI images) and an anatomical image 3 with high contrast and high resolution. The neurological disorder may include neurodegenerative diseases, e.g., Parkinson's disease (PD), Alzheimer's disease (AD) and the like, or neurodevelopmental disorders, e.g., cerebral palsy (CP) and the like, but is not limited thereto. The method is to be implemented by a computing device having computational capability, such as a workstation computer, a personal computer, a tablet computer, or the like, but is not limited thereto. The method includes the following steps 11-14.

Referring to FIGS. 1A and 1B, step 11 includes sub-steps 111-113 described as follows.

In sub-step 111, the computing device performs image processing on the diffusion MRI images 2 to result in at least one diffusion index. Specifically, said at least one diffusion index is generated by fitting a diffusion model to the diffusion MRI images 2. Said at least one diffusion index is defined by a plurality of diffusion index values. In one embodiment, said at least one diffusion index may be formatted as an image, and an individual one of the diffusion index values is implemented to be a pixel value of a pixel in the aforementioned image. The image processing (i.e., the diffusion model adopted for fitting) is one of diffusion tensor imaging (DTI), diffusion kurtosis imaging (DKI), neurite orientation dispersion and density imaging (NODDI), and the AxCaliber technique which is an expansion to the composite hindered and restricted model of diffusion (CHARMED) framework. Specifically speaking, said at least one diffusion index resulting from DTI is one of fractional anisotropy (FA), mean diffusivity (MD), radial diffusivity (RD) and axial diffusivity (AXD); said at least one diffusion index resulting from DKI is one of kurtosis fractional anisotropy (KFA), mean kurtosis (MK), radial kurtosis (KR) and axial kurtosis (KA); the diffusion index resulting from NODDI is one of intra-cellular volume fraction (Ficvf), cerebrospinal fluid volume fraction (Fiso), fitting objective function values (Fmin), concentration parameter of Watson distribution (Fkappa) and orientation dispersion index (ODI); and said at least one diffusion index resulting from the AxCaliber technique is one of signal decay of the hindered diffusion fraction of water molecules (Eh) and signal decay of the restricted diffusion fraction of water molecules (Er). For example, two diffusion indexes that are respectively MD and FA can be obtained by fitting DTI to the diffusion MRI images 2, and can be formatted as two images which are simply referred to as MD (22) and FA (23) herein, respectively.

Subsequently, said at least one diffusion index is normalized based on the anatomical image 3 and a structural template 6 (see FIG. 2) in sub-step 112, and is then parcellated through automatic whole-brain parcellation in sub-step 113 according to a standard brain parcellation template 5, e.g., an automated anatomical labeling (AAL) template as shown in FIG. 2, so that a plurality of brain image regions 4 are identified thereon. In this embodiment, the brain image regions 4 are one hundred and sixteen in number, but implementation of the number of the brain image regions 4 is not limited to what are disclosed herein. Each of the brain image regions 4 contains a respective portion of the diffusion index values (i.e., the pixel values of pixels corresponding to the brain image region) of said at least one diffusion index.

It should be noted that the normalizing of said at least one diffusion index is performed spatially, and implementation thereof is not limited to what are disclosed herein and may vary in other embodiments.

In step 12, a statistical transformation, which is associated with a normal distribution, is performed on the diffusion index values of said at least one diffusion index thus normalized and parcellated to result in transformed index values. In one embodiment, an individual one of the transformed index values may be implemented to be a pixel value of a pixel in another image resulting from performance of the statistical transformation on the aforementioned image (e.g., MD or FA) thus normalized and parcellated. In this embodiment, the statistical transformation is implemented by a Box-Cox transformation, but is not limited thereto.

In one embodiment, the Box-Cox transformation is performed over the whole of the diffusion index values of all of the brain image regions 4 to result in the transformed index values so that distribution of the transformed index values of all of the brain regions approaches a normal distribution.

In one embodiment, for each of the brain image regions 4, the Box-Cox transformation is performed over the portion of the diffusion index values corresponding to the brain image region 4 to result in the transformed index values so that distribution of the transformed index values corresponding to the brain image region 4 approaches a normal distribution.

In step 13, for each of the brain image regions 4, at least one characteristic parameter is calculated based on a portion of the transformed index values corresponding to the brain image region 4. For each of the brain image regions 4, said at least one characteristic parameter includes a statistical value of the portion of the transformed index values corresponding to the brain image region 4. In this embodiment, the statistical value may be implemented to be one of a mean and a percentile, e.g., a $10^{th}$ percentile, a $50^{th}$ percentile, a $90^{th}$ percentile or the like, but is not limited thereto. Furthermore, the characteristic parameters of the brain image regions 4 belonging to at least one targeted type of statistic calculation are selected to form a feature matrix, which is a combination of the characteristic parameters of the brain image regions 4 calculated according to the targeted type of statistic calculation. For instance, for each of the one hundred and sixteen brain image regions 4, four characteristic parameters (i.e., the mean, the $10^{th}$ percentile, the $50^{th}$ percentile and the $90^{th}$ percentile) are calculated in step 13, and if two of the four characteristic parameters of each of the brain image regions 4 are selected to form the feature matrix (e.g., the at least one targeted type of statistical calculation includes calculation of the mean and the $10^{th}$ percentile), the feature matrix includes 2×116 characteristic parameters in total.

In step 14, the brain examined is diagnosed with one of predetermined categories of the neurological disorder by performing classification on the feature matrix via a classifier that is trained in advance and that is associated with the predetermined categories of the neurological disorder. In this embodiment, the classifier may be implemented to be one of a support vector machine, an artificial neural network, a discriminant function analysis, or the like, but is not limited thereto.

For example, in order to diagnose cerebral palsy (CP) via the classifier, two categories representing respectively a normal case and a CP case are defined in advance, and for each of the two categories, a plurality of training samples corresponding there to are collected for training the classifier. That is to say, for each individual in a group of normal people, a plurality of diffusion MRI images 2 and an anatomical image 3 that are associated with a brain of the individual are collected to serve as one of the training samples for the normal case. Likewise, for each individual in a group of CP patients, another plurality of diffusion MRI images 2 and another anatomical image 3 that are associated with a brain of the individual are collected to serve as one of the training samples for the CP case. Thereafter, according to steps 11-14 mentioned previously, feature matrices corresponding to the training samples are thereby calculated and are utilized to train the classifier. After the classifier has been trained, a feature matrix that is associated with a brain examined can be classified by the classifier so that the brain examined can be diagnosed as one of a normal case and a CP case.

It should be noted that performing the statistical transformation (e.g., the Box-Cox transformation) on the diffusion index values of said at least one diffusion index thus normalized and parcellated is a step for the method of this disclosure which enhances discrimination of the feature matrix thus calculated and improves correctness of classification by the classifier. In one embodiment, step 12 of performing the statistical transformation on the diffusion index values of said at least one diffusion index thus normalized and parcellated can be omitted. Moreover, the order of performing the statistical transformation in the method of this disclosure is not limited to what are disclosed herein, and may vary in other embodiments. For example, the statistical transformation may be performed on the feature matrix formed in step 13.

Figure 15:
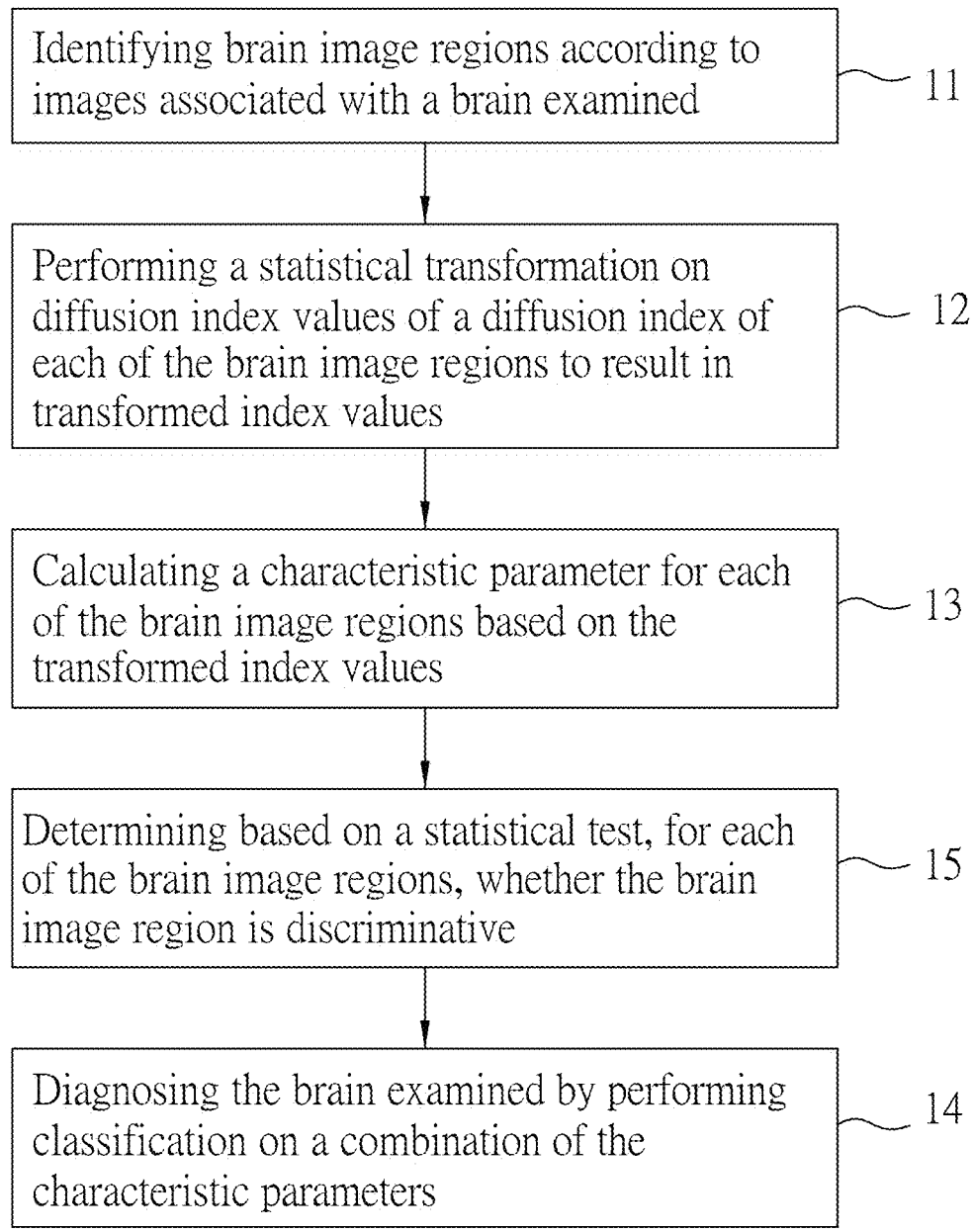
FIG. 15 is a flow diagram illustrating a variation of the embodiment of the method according to the disclosure.

In a variation of this embodiment, referring to FIG. 15, the method of this disclosure further includes, prior to step 14, step 15 in which the computing device determines based on a statistical test, for each of the brain image regions 4, whether the respective brain image region 4 is discriminative for the categories of the neurological disorder. Subsequently, in step 14, classification is performed on the combination (i.e., the feature matrix) of the characteristic parameters of the brain image regions 4 which are determined to be discriminative for the categories of the neurological disorder via the classifier.

In one embodiment, prior to diagnosing the neurological disorder in the brain examined, the statistical test is performed based on the training samples of the categories, so as to determine, for each of the brain image regions 4, whether a characteristic parameter of the respective brain image region 4 is discriminative for the categories of the neurological disorder. For instance, referring to FIG. 2, for the brain image region R of each of the training samples, the statistical test is performed thereon so as to determine whether the brain image region (R) is discriminative for the categories of the neurological disorder. In other words, when it is determined by the statistical test that for one of the training samples in each of the categories, the characteristic parameter of the brain image region (R) comes from an identical population, the characteristic parameter of the brain image region (R) will be determined as non-discriminative. Otherwise, when it is determined by the statistical test that for one of the training samples in each of categories, the characteristic parameter of the brain image region (R) does not come from the same population, the characteristic parameter of the brain image region (R) will be determined as discriminative. Therefore, when only those of the characteristic parameters which are determined to be discriminative for the categories are kept to constitute a feature matrix for a corresponding one of the training samples (or for the brain examined), dimensions of the feature matrix can be effectively reduced without adversely influencing correctness of classification, and the amount of computation by the computing device for diagnosing the neurological disorder in the brain examined is thereby reduced. When a number of the categories of the neurological disorder is two, the statistical test may be implemented by a Mann-Whitney U test so as to determine whether a characteristic parameter of each of the brain image regions 4 is discriminative for the categories of the neurological disorder. When the number of the categories of the neurological disorder is greater than two, the statistical test may be implemented by a Kruskal-Wallis test.

It is worth noting that in a scenario where diagnosis is made based on training samples in each of the categories, the statistical transformation may be implemented in an alternative way by performing, for each of the categories of the neurological disorder, the Box-Cox transformation on the feature matrices of the training samples in the category so that a distribution of the feature matrices thus transformed approaches a normal distribution. Next, classification is performed using the classifier on the feature matrices thus transformed for diagnosing the neurological disorder.

To verify effectiveness of the method of this disclosure, a plurality of samples associated with different neurological disorders are collected and analyzed. Specifically speaking, for each of the neurological disorders, three different approaches of performing the statistical transformation (e.g., the Box-Cox transformation) are applied, and different implementations of the characteristic parameters are adopted for experimental analysis. The three approaches of performing the statistical transformation are respectively described in the following three paragraphs.

For the first approach, for each of the brain image regions 4, the Box-Cox transformation is performed over the portion of the diffusion index values corresponding to the brain image region 4 to result in the transformed index values.

For the second approach, the Box-Cox transformation is performed over the whole of the diffusion index values of all of the brain image regions 4 to result in the transformed index values.

For the third approach, for each of the categories of the neurological disorder, the Box-Cox transformation is performed on the feature matrices corresponding to the category.

For convenience of explanation, four tasks of diagnosing a neurological disorder are respectively described in the following four paragraphs.

The first task aims for diagnosing Parkinson's disease (PD) which includes four categories, where category one represents a normal case, category two represents a multiple system atrophy (MSA) case, category three represents a progressive supranuclear palsy (PSP) case, and category four represents an idiopathic PD (IPD) case.

The second task aims for diagnosing Alzheimer's disease (AD) which includes three categories, where category one represents a normal case, category two represents a mild cognitive impairment (MCI) case, and category three represents an AD case.

The third task aims for evaluating whether a MCI case will progress to an AD case, and a result of the evaluation includes two categories, where category one represents that the MCI case will not progress to the AD case, and category two represents that the MCI case will progress to the AD case.

The fourth task aims for diagnosing cerebral palsy (CP) which includes two categories, where category one represents a normal case, and category two represents a CP case.

Figure 3:
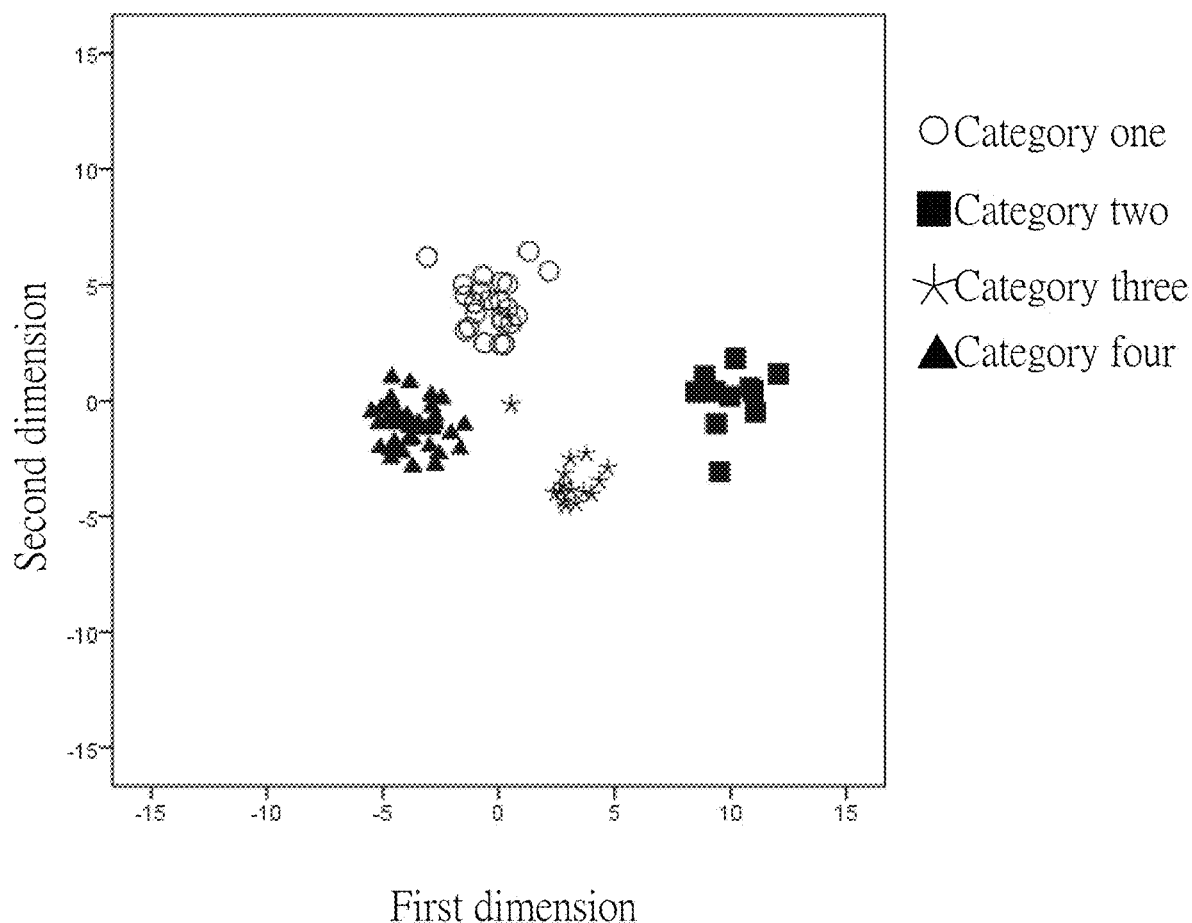
FIG. 3 is a scatter plot exemplifying that a plurality of samples are classified into four categories and are presented in a two-dimensional data presentation.

For the first task (i.e., PD diagnosis), FIG. 3 illustrates a result of classification where the first approach is adopted and characteristic parameters of brain image regions are implemented by an MD mean (i.e., a mean of transformed index values of MD), a FA mean (i.e., a mean of transformed index values of FA) and an AXD mean (i.e., a mean of transformed index values of AxD). The result shows that most samples can be clearly classified into the four categories in a two-dimensional data presentation when dimensions of feature matrices respectively corresponding to the samples are reduced to two by the discriminant function analysis.

Furthermore, a leave-one-out cross validation is utilized to validate performance of the first approach in the first task, where the characteristic parameters of the brain image regions are implemented by the MD mean, the FA mean and the AXD mean. Specifically speaking, the feature matrices of respective samples take turns being used for test, while the remaining ones of the feature matrices other than the feature matrix used for test are used for training the classifier. As each of the feature matrices of the samples has been used for test once, a result of the leave-one-out cross validation can be obtained as shown in Table 1. The result shows that a 98.8% correctness of classification in the first task can be achieved by the first approach, where only one out of ninety-two samples is incorrectly classified, i.e., a sample that is actually a normal case is incorrectly classified as an IPD case.

TABLE 1 classification by the first approach in the first task

| | Actual | | | | |
|---|---|---|---|---|---|
| Classified | Normal | MSA | PSP | IPD | Total count |
| Normal | 22 | 0 | 0 | 1 | 23 |
| MSA | 0 | 12 | 0 | 0 | 12 |
| PSP | 0 | 0 | 15 | 0 | 15 |
| IPD | 0 | 0 | 0 | 42 | 42 |

Figure 4:
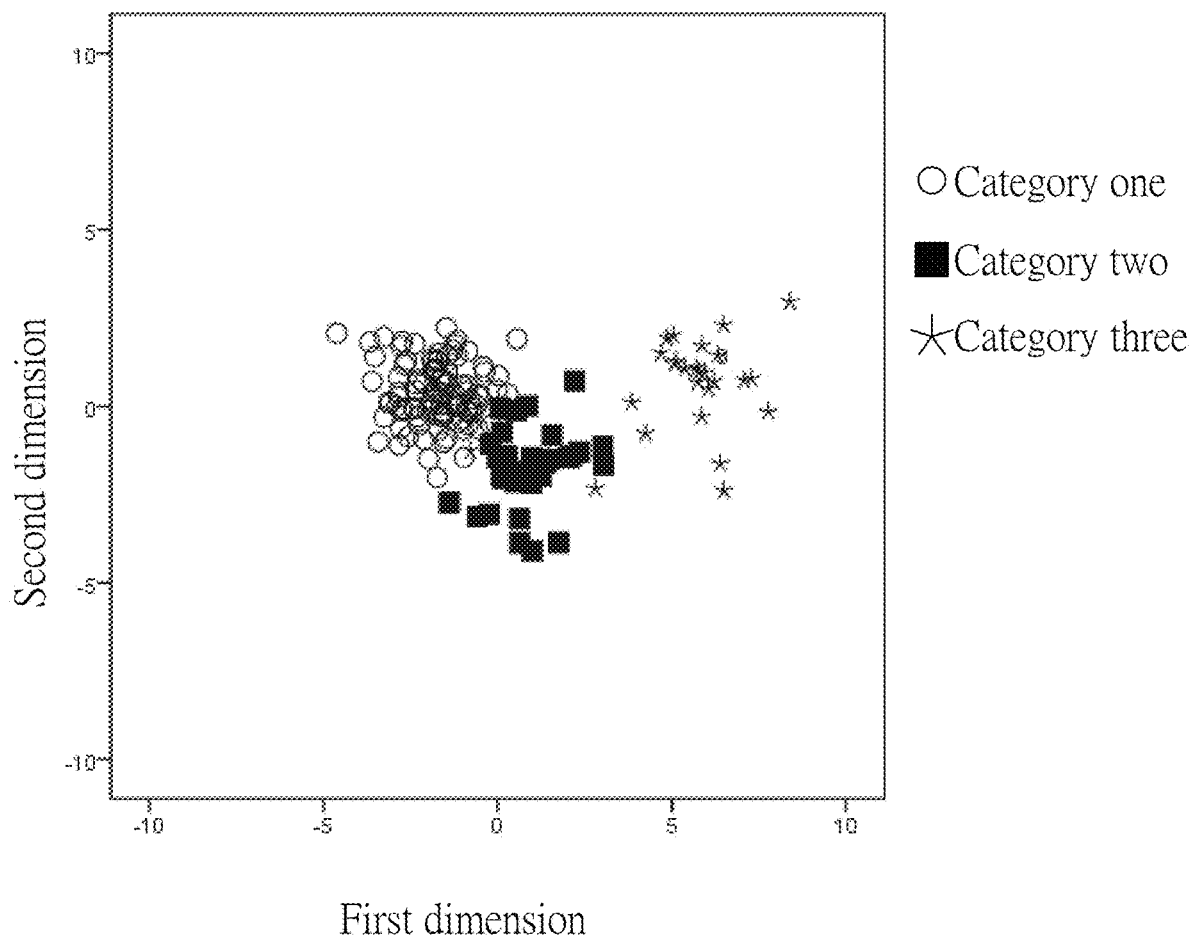
FIG. 4 is a scatter plot exemplifying that a plurality of samples are classified into three categories in a two-dimensional data presentation.

Similarly, FIG. 4 illustrates a result of classification in the second task (i.e., AD diagnosis) where the first approach is adopted and where characteristic parameters of brain image regions are implemented by the MD mean, the FA mean and the AXD mean. Table 2 below shows a result of the leave-one-out cross validation corresponding thereto. The result of the leave-one-out cross validation shows that a 91.1% correctness of classification in the second task can be achieved by the first approach.

TABLE 2 classification by the first approach in the second task

| | Actual | | | |
|---|---|---|---|---|
| Classified | Normal | MCI | AD | Total count |
| Normal | 91 | 8 | 0 | 99 |
| MCI | 2 | 29 | 1 | 32 |
| AD | 1 | 2 | 23 | 26 |

Figure 5:
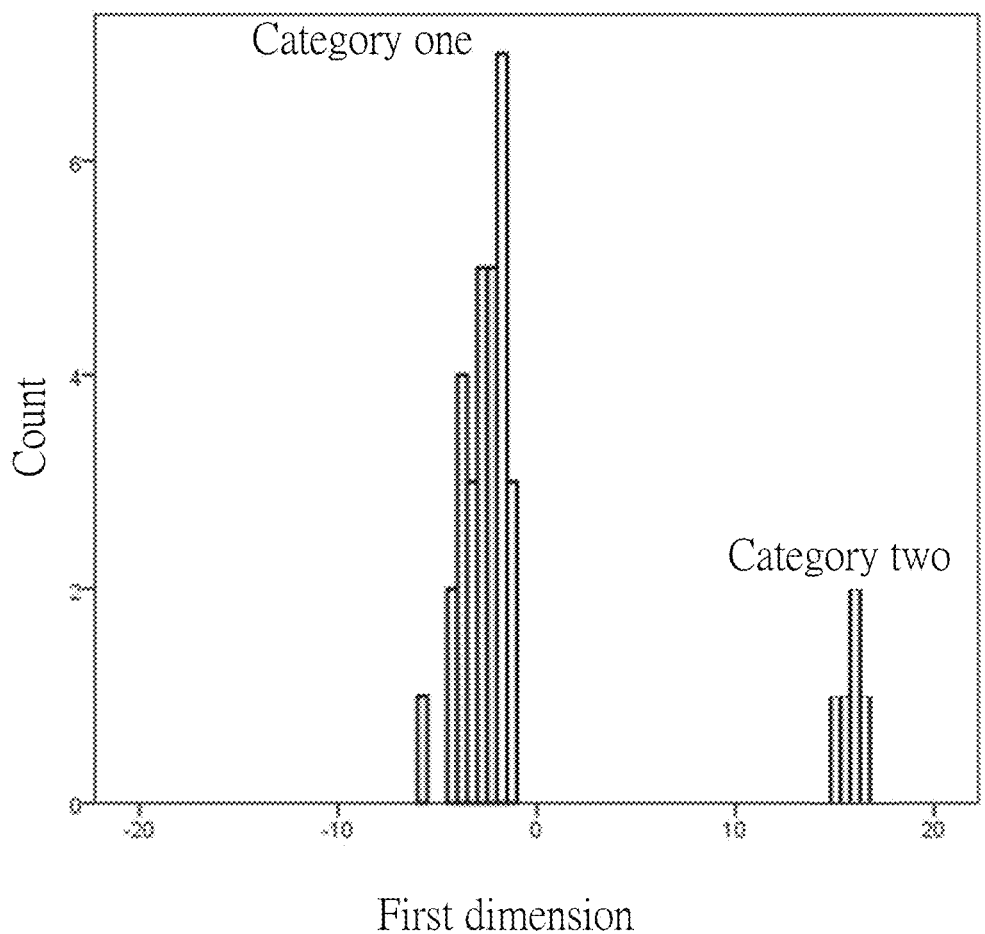
FIG. 5 is a histogram exemplifying that a plurality of samples are classified into two categories in a one-dimensional feature space.

For the third task (i.e., evaluating whether a MCI case will progress to an AD case), FIG. 5 illustrates a result of classification where the first approach is adopted and characteristic parameters of brain image regions are implemented by the MD mean. The result shows that most samples can be clearly classified into the two categories in a one-dimensional feature space when dimensions of feature matrices respectively corresponding to the samples are reduced to one by the discriminant function analysis.

Additionally, the leave-one-out cross validation is utilized to validate performance of the first approach in the third task, where the characteristic parameters of the brain image regions are implemented by the MD mean. A result of the leave-one-out cross validation is obtained as shown in Table 3. The result shows that a 100% correctness of classification in the third task is achieved by the first approach.

TABLE 3 classification by the first approach in the third task

| | Actual | | |
|---|---|---|---|
| Classified | Will not progress to AD | Will progress to AD | Total count |
| Will not progress to AD | 30 | 0 | 30 |
| Will progress to AD | 0 | 5 | 5 |

Figure 6:
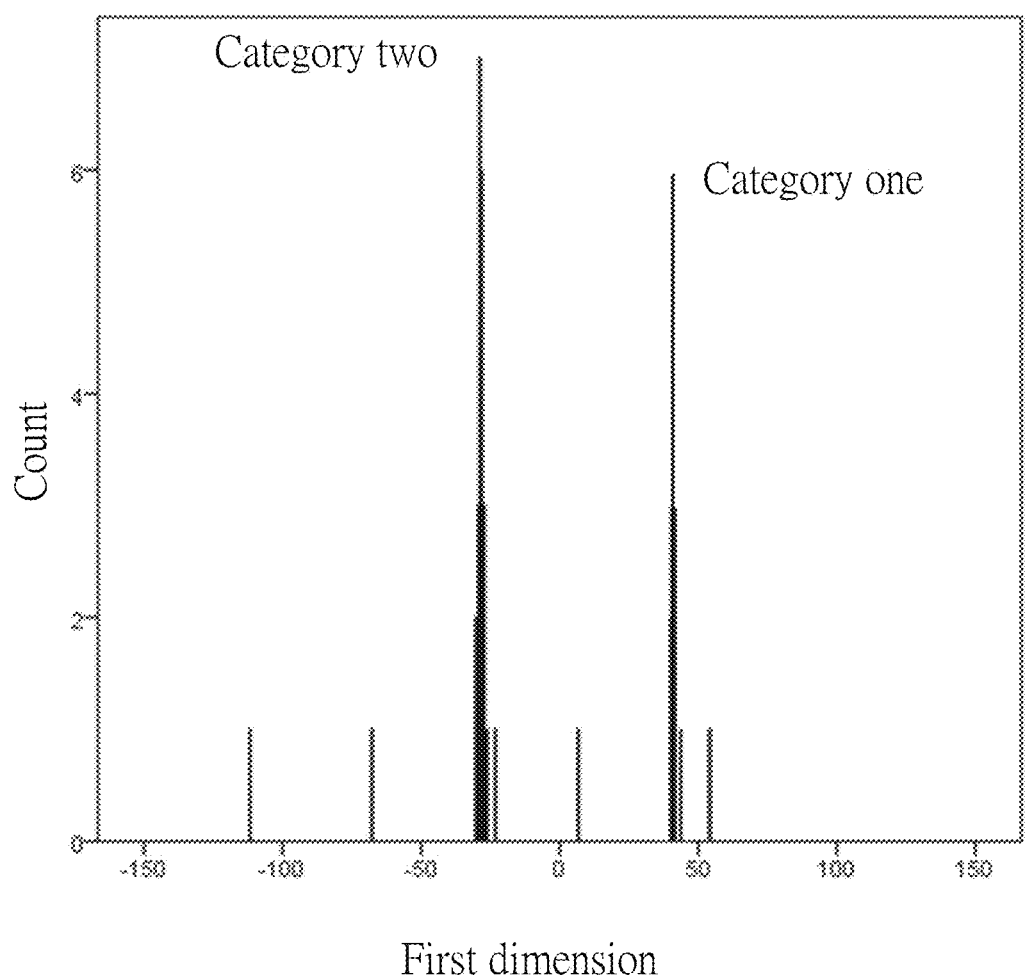
FIG. 6 is a histogram exemplifying that a plurality of samples are classified into two categories in a one-dimensional feature space.

For the fourth task (i.e., CP diagnosis), FIG. 6 illustrates a result of classification where the first approach is adopted and characteristic parameters of brain image regions are implemented by the FA mean and a $10^{th}$ MD percentile (i.e., a $10^{th}$ percentile of transformed index values of MD). The result shows that most samples can be clearly classified into the two categories in a one-dimensional feature space when dimensions of feature matrices respectively corresponding to the samples are reduced to one by the discriminant function analysis.

In addition, the leave-one-out cross validation is utilized to validate performance of the first approach in the fourth task, where the characteristic parameters of the brain image regions are implemented by the FA mean and the $10^{th}$ MD percentile. A result of the leave-one-out cross validation is obtained as shown in Table 4. The result shows that a 98% correctness of classification in the fourth task is achieved by the first approach.

TABLE 4 classification by the first approach in the fourth task

| | Actual | | |
|---|---|---|---|
| Classified | Normal | CP | Total count |
| Normal | 20 | 0 | 20 |
| CP | 1 | 30 | 31 |

Figure 7:
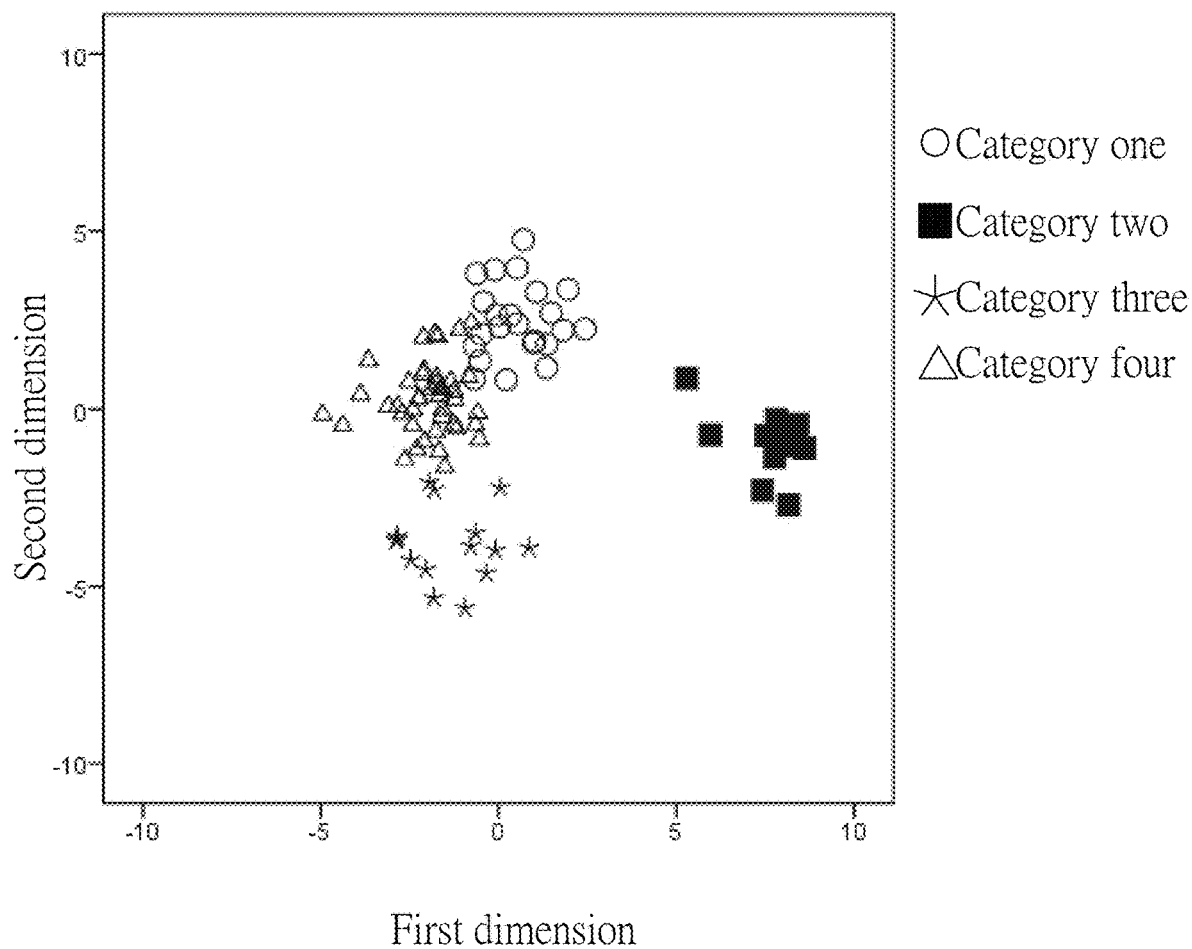
FIG. 7 is a scatter plot exemplifying that a plurality of samples are classified into four categories and are presented in a two-dimensional data presentation.

For the first task (i.e., PD diagnosis), FIG. 7 illustrates a result of classification where the second approach is adopted and characteristic parameters of brain image regions are implemented by the $10^{th}$ MD percentile, an $50^{th}$ FA percentile (i.e., a $50^{th}$ percentile of transformed index values of FA) and a $90^{th}$ FA percentile (i.e., a $90^{th}$ percentile of transformed index values of FA). The result shows that most samples can be clearly classified into the four categories in a two-dimensional data presentation when dimensions of feature matrices respectively corresponding to the samples are reduced to two by the discriminant function analysis.

In addition, the leave-one-out cross validation is utilized to validate performance of the second approach in the first task, where the characteristic parameters of brain image regions are implemented by the $10^{th}$ MD percentile, the $50^{th}$ FA percentile and the $90^{th}$ FA percentile. A result of the leave-one-out cross validation is obtained as shown in Table 5. The result shows that a 85.9% correctness of classification in the first task is achieved by the second approach.

TABLE 5 classification by the second approach in the first task

|  | Actual | | | | |
| --- | --- | --- | --- | --- | --- |
| Classified | Normal | MSA | PSP | IPD | Total count |
| Normal | 22 | 0 | 0 | 1 | 23 |
| MSA | 2 | 10 | 0 | 0 | 12 |
| PSP | 0 | 0 | 10 | 5 | 15 |
| IPD | 4 | 0 | 1 | 37 | 42 |

Figure 8:
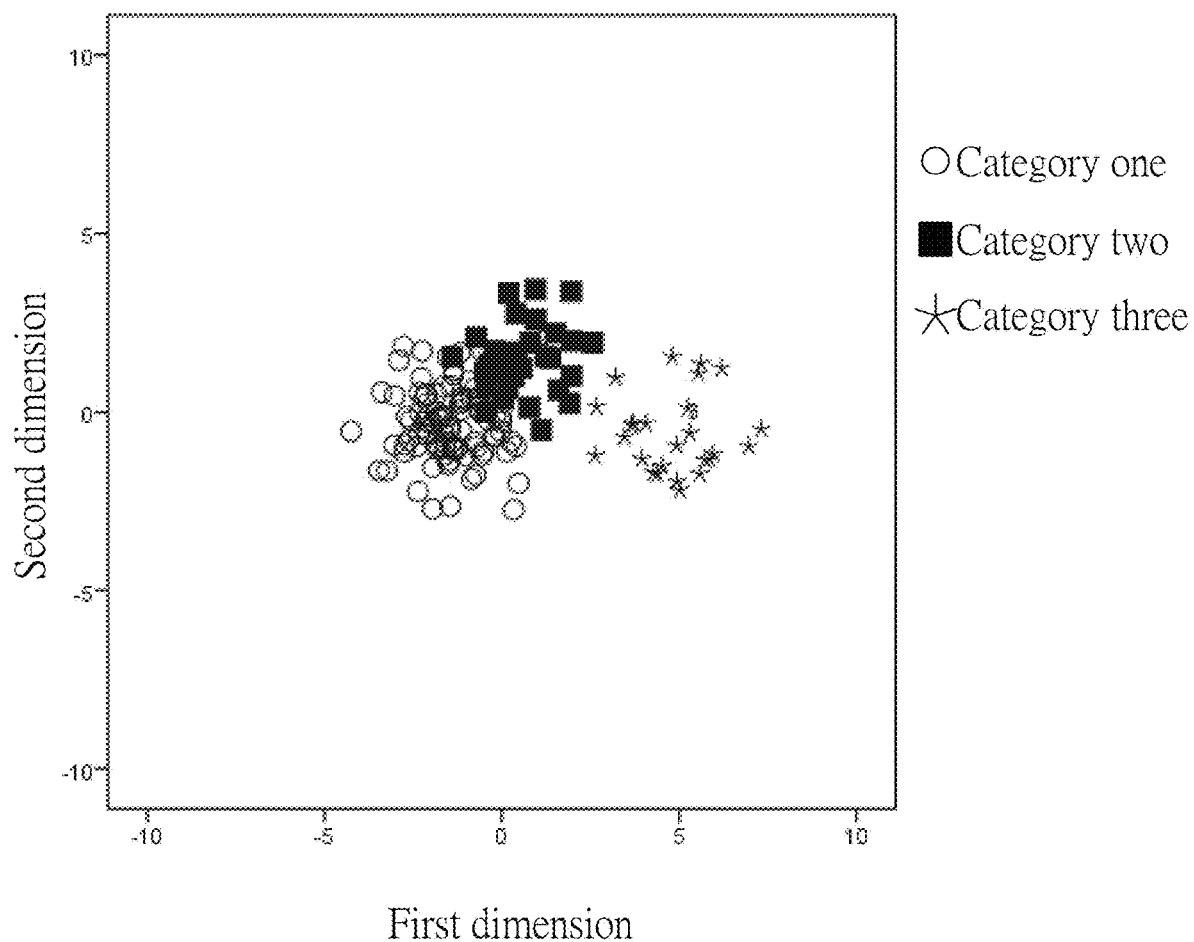
FIG. 8 is a scatter plot exemplifying that a plurality of samples are classified into three categories and are presented in a two-dimensional data presentation.

Similarly, FIG. 8 illustrates a result of classification in the second task (i.e., AD diagnosis) where the second approach is adopted and where characteristic parameters of brain image regions are implemented by the MD mean, the FA mean and the AXD mean. Table 6 below shows a result of the leave-one-out cross validation corresponding thereto. The result of the leave-one-out cross validation shows that a 86% correctness of classification in the second task can be achieved by the second approach.

TABLE 6 classification by the second approach in the second task

|  | Actual | | | |
| --- | --- | --- | --- | --- |
| Classified | Normal | MCI | AD | Total count |
| Normal | 85 | 14 | 0 | 99 |
| MCI | 6 | 26 | 0 | 32 |
| AD | 0 | 2 | 24 | 26 |

Figure 9:
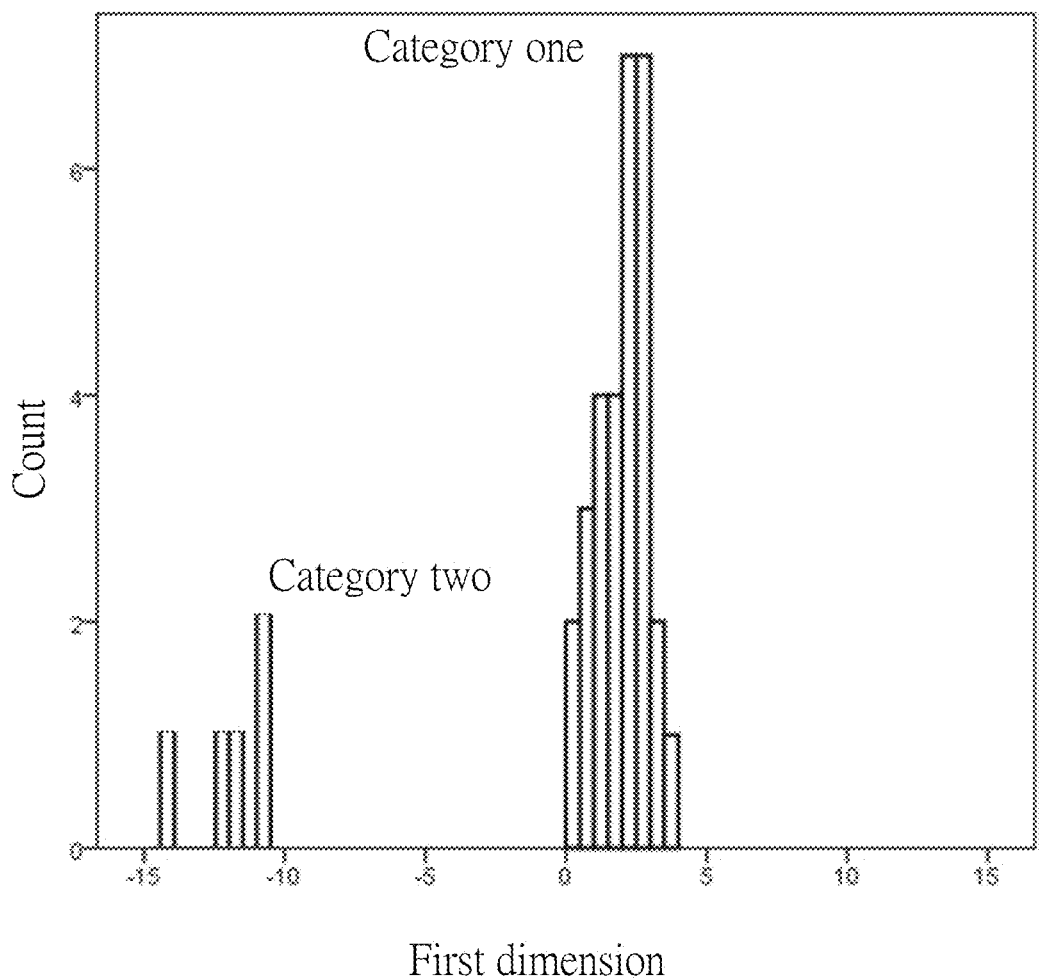
FIG. 9 is a histogram exemplifying that a plurality of samples are classified into two categories in a one-dimensional feature space.

For the third task (i.e., evaluating whether a MCI case will progress to an AD case), FIG. 9 illustrates a result of classification where the second approach is adopted and characteristic parameters of brain image regions are implemented by the AXD mean. The result shows that most samples can be clearly classified into the two categories in a one-dimensional feature space when dimensions of feature matrices respectively corresponding to the samples are reduced to one by the discriminant function analysis.

Additionally, the leave-one-out cross validation is utilized to validate performance of the second approach in the third task, where the characteristic parameters of the brain image regions are implemented by the AXD mean. A result of the leave-one-out cross validation is obtained as shown in Table 7. The result shows that a 100% correctness of classification in the third task is achieved by the second approach.

TABLE 7 classification by the second approach in the third task

|  | Actual | | |
| --- | --- | --- | --- |
| Classified | Will not progress to AD | Will progress to AD | Total count |
| Will not progress to AD | 30 | 0 | 30 |
| Will progress to AD | 0 | 5 | 5 |

Figure 10:
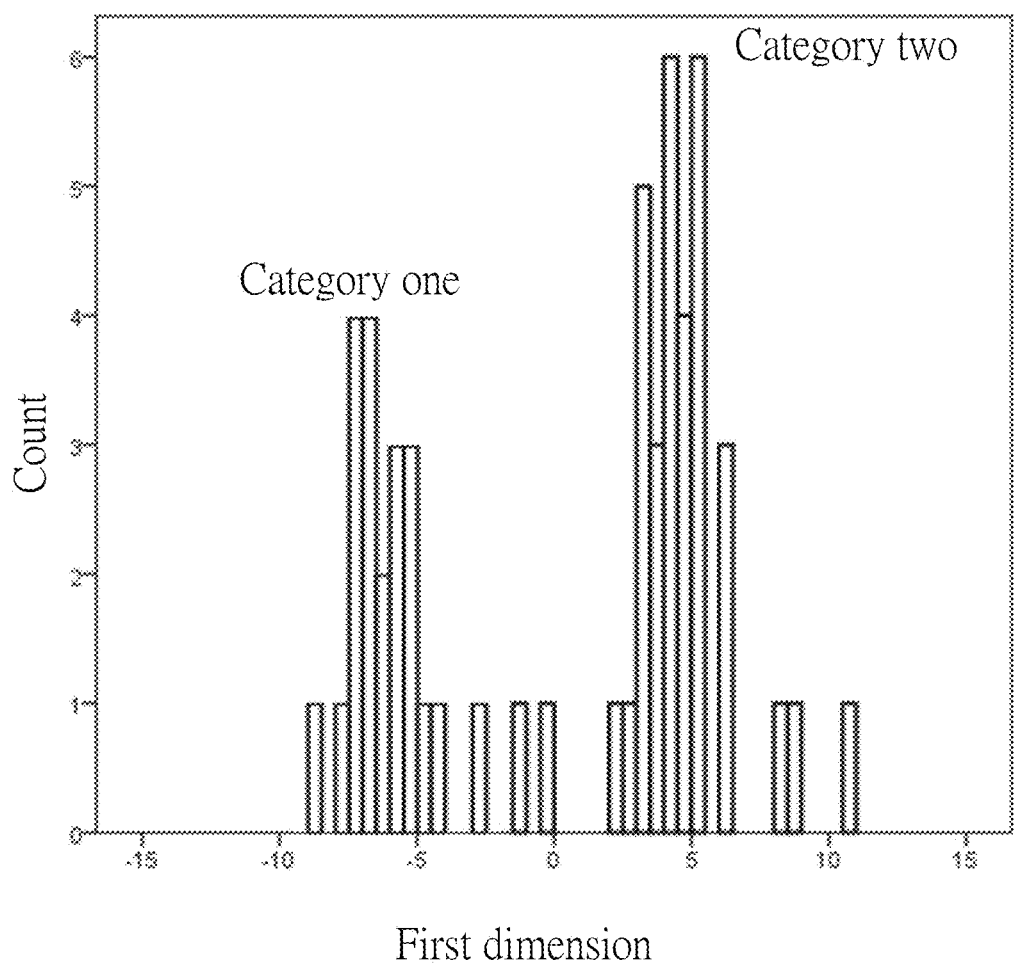
FIG. 10 is a histogram exemplifying that a plurality of samples are classified into two categories in a one-dimensional feature space.

For the fourth task (i.e., CP diagnosis), FIG. 10 illustrates a result of classification where the second approach is adopted and characteristic parameters of brain image regions are implemented by the FA mean and the $10^{th}$ MD percentile. The result shows that most samples can be clearly classified into the two categories in a one-dimensional feature space when dimensions of feature matrices respectively corresponding to the samples are reduced to one by the discriminant function analysis.

In addition, the leave-one-out cross validation is utilized to validate performance of the second approach in the fourth task, where the characteristic parameters of the brain image regions are implemented by the FA mean and the $10^{th}$ MD percentile. A result of the leave-one-out cross validation is obtained as shown in Table 8. The result shows that a 94.7% correctness of classification in the fourth task is achieved by the second approach.

TABLE 8 classification by the second approach in the fourth task

|  | Actual | | |
| --- | --- | --- | --- |
| Classified | Normal | CP | Total count |
| Normal | 21 | 1 | 22 |
| CP | 2 | 33 | 35 |

Figure 11:
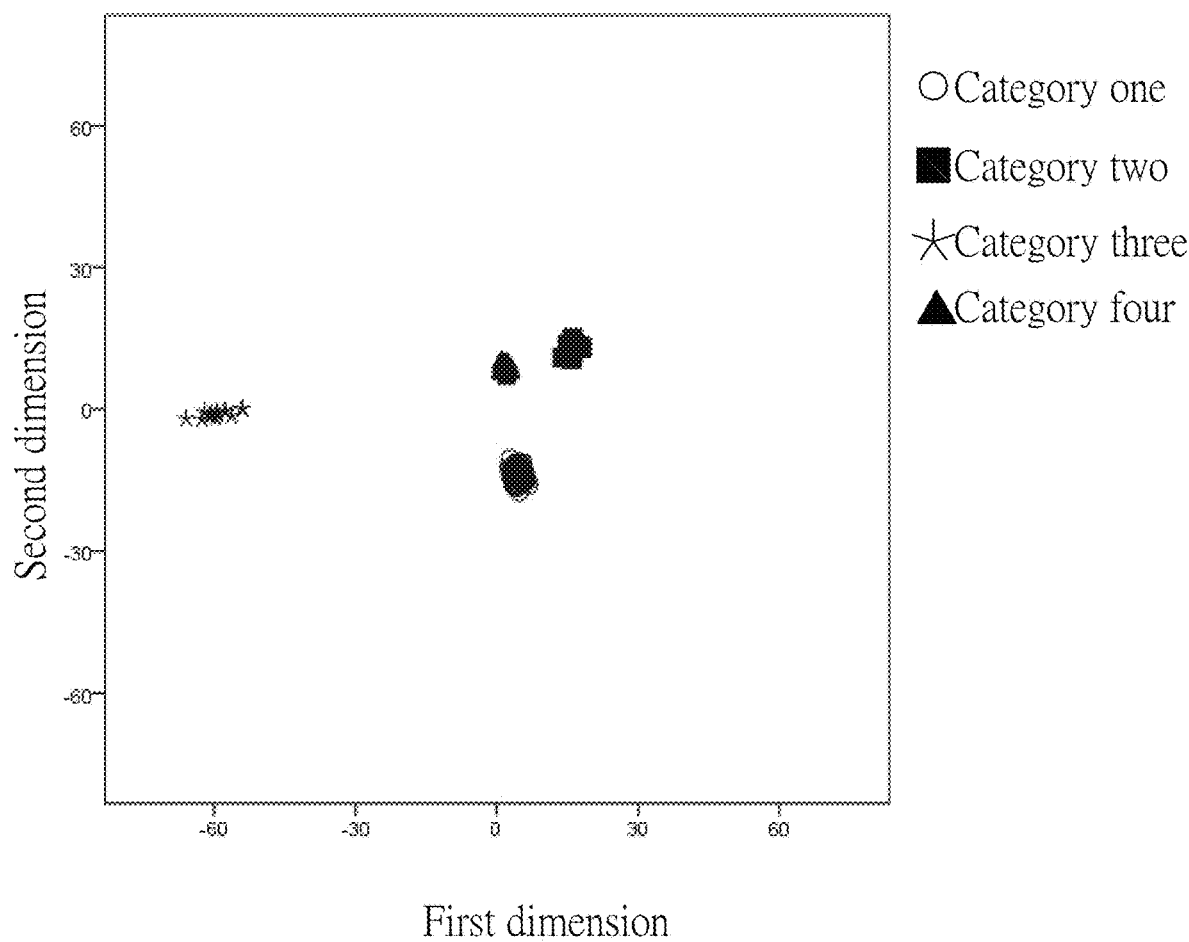
FIG. 11 is a scatter plot exemplifying that a plurality of samples are classified into four categories in a two-dimensional data presentation.

For the first task (i.e., PD diagnosis), FIG. 11 illustrates a result of classification where the third approach is taken and characteristic parameters of brain image regions are implemented by a $50^{th}$ FA percentile (i.e., a $50^{th}$ percentile of diffusion index values of FA). The result shows that most samples can be clearly classified into the four categories in a two-dimensional data presentation when dimensions of feature matrices respectively corresponding to the samples are reduced to two by the discriminant function analysis.

Furthermore, the leave-one-out cross validation is utilized to validate performance of the third approach in the first task, where the characteristic parameters of the brain image regions are implemented by the $50^{th}$ FA percentile. A result of the leave-one-out cross validation is obtained as shown in Table 9. The result shows that a 100% correctness of classification in the first task is achieved by the third approach.

TABLE 9 classification by the third approach in the first task

| | Actual | | | | |
|---|---|---|---|---|---|
| Classified | Normal | MSA | PSP | IPD | Total count |
| Normal | 96 | 0 | 0 | 0 | 96 |
| MSA | 0 | 15 | 0 | 0 | 15 |
| PSP | 0 | 0 | 15 | 0 | 15 |
| IPD | 0 | 0 | 0 | 135 | 135 |

Figure 12:
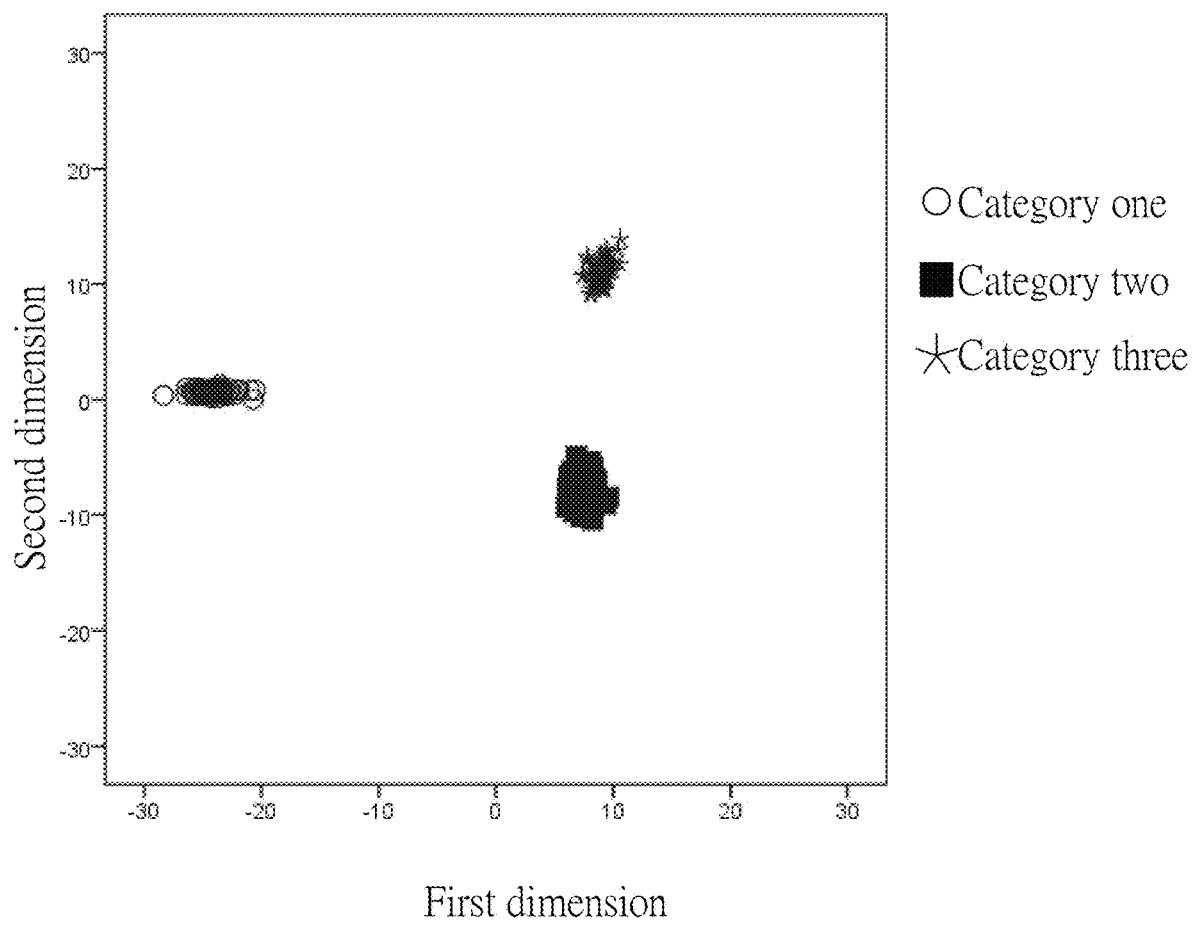
FIG. 12 is a scatter plot exemplifying that a plurality of samples are classified into three categories in a two-dimensional data presentation.

Similarly, FIG. 12 illustrates a result of classification in the second task (i.e., AD diagnosis) where the third approach is adopted and where characteristic parameters of brain image regions are implemented by the 50$^{th}$ FA percentile, and Table 10 below shows a result of the leave-one-out cross validation corresponding thereto. The result of the leave-one-out cross validation shows that a 100% correctness of classification in the second task can be achieved by the third approach.

TABLE 10 classification by the third approach in the second task

| | Actual | | | |
|---|---|---|---|---|
| Classified | Normal | MCI | AD | Total count |
| Normal | 44 | 0 | 0 | 44 |
| MCI | 0 | 79 | 0 | 79 |
| AD | 0 | 0 | 53 | 53 |

Figure 13:
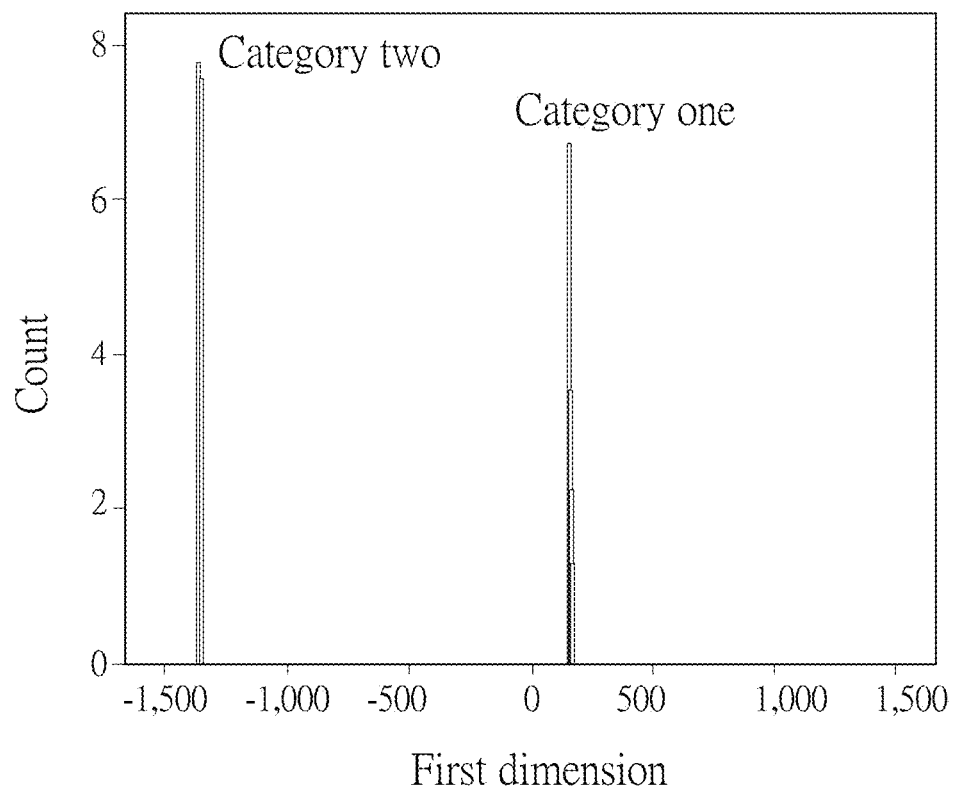
FIG. 13 is a histogram exemplifying that a plurality of samples are classified into two categories in a one-dimensional feature space.

For the third task (i.e., evaluating whether a MCI case will progress to an AD case), FIG. 13 illustrates a result of classification where the third approach is adopted and characteristic parameters of brain image regions are implemented by the 50$^{th}$ FA percentile. The result shows that most samples can be clearly classified into the two categories in a one-dimensional data presentation when dimensions of feature matrices respectively corresponding to the samples are reduced to one by the discriminant function analysis.

Additionally, the leave-one-out cross validation is utilized to validate performance of the third approach in the third task, where the characteristic parameters of the brain image regions are implemented by the 50$^{th}$ FA percentile. A result of the leave-one-out cross validation is obtained as shown in Table 11. The result shows that a 100% correctness of classification in the third task is achieved by the third approach.

TABLE 11 classification by the third approach in the third task

| | Actual | | |
|---|---|---|---|
| Classified | Will not progress to AD | Will progress to AD | Total count |
| Will not progress to AD | 72 | 0 | 72 |
| Will progress to AD | 0 | 8 | 8 |

Figure 14:
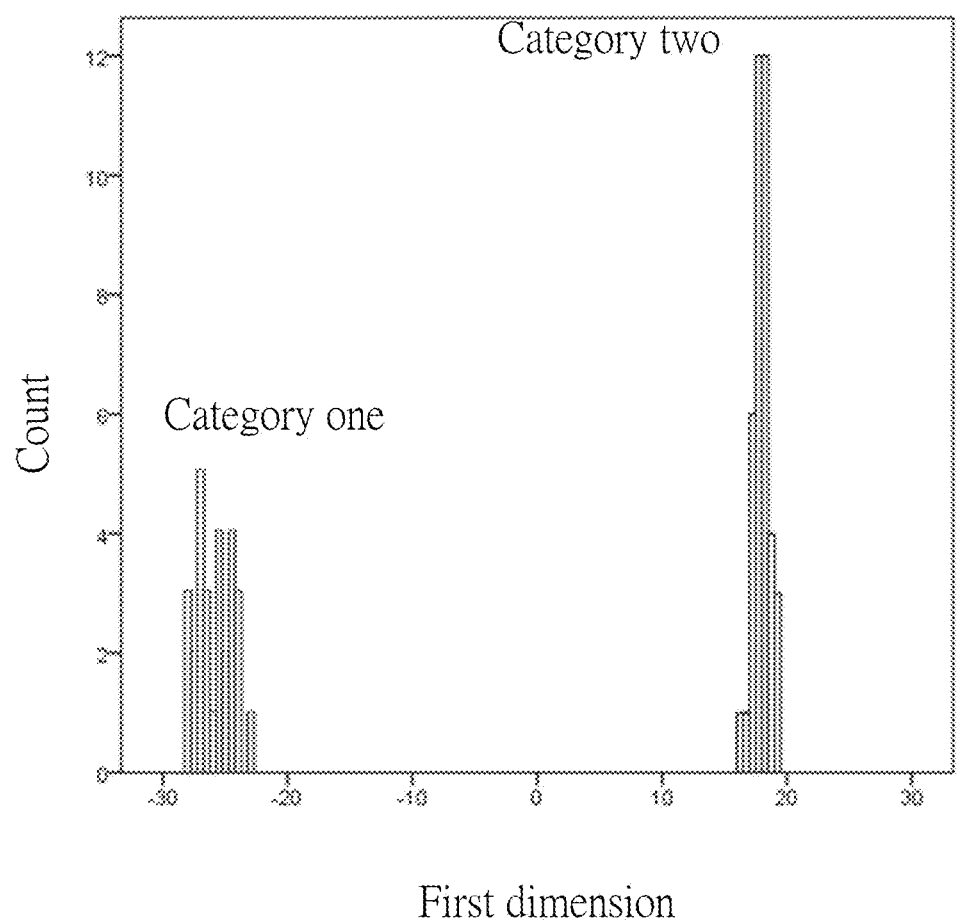
FIG. 14 is a histogram exemplifying that a plurality of samples are classified into two categories in a one-dimensional feature space.

For the fourth task (i.e., CP diagnosis), FIG. 14 illustrates a result of classification where the third approach is adopted and characteristic parameters of brain image regions are implemented by the 50$^{th}$ FA percentile. The result shows that most samples can be clearly classified into the two categories in a one-dimensional feature space when dimensions of feature matrices respectively corresponding to the samples are reduced to one by the discriminant function analysis.

In addition, the leave-one-out cross validation is utilized to validate performance of the third approach in the fourth task. A result of the leave-one-out cross validation is obtained as shown in Table 12. The result shows that a 100% correctness of classification in the fourth task is achieved by the third approach.

TABLE 12 classification by the third approach in the fourth task

| | Actual | | |
|---|---|---|---|
| Classified | Normal | CP | Total count |
| Normal | 28 | 0 | 28 |
| CP | 0 | 39 | 39 |

Although only results of classification by using the discriminant function analysis are provided in the aforementioned experimental analysis, other classifiers such as the support vector machine or the artificial neural network may be utilized to achieve substantially high correctness of classification as well, and descriptions of experiments thereof are omitted herein for the sake of brevity.

In summary, the method of this disclosure includes identifying brain image regions according to diffusion MRI images and an anatomical image that are associated with a brain examined, and performing the Box-Cox transformation on diffusion index values of the brain image regions to result in transformed index values. In addition, for each of the brain image regions, the method further includes calculating at least one characteristic parameter based on the respective portion of the transformed index values, and diagnosing the brain examined with one of predetermined categories of the neurological disorder by performing classification, via a classifier previously trained, on a feature matrix which is constituted by the characteristic parameters. As a result, neurological disorders can be effectively and correctly diagnosed.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included with in the spirit and scope of the broadest interpretation so as to encompass all such modifications and equivalent arrangements.

What is claimed is:

1. A method for diagnosing a neurological disorder based on at least one magnetic resonance imaging (MMI) image that is associated with a brain examined, said method to be implemented by a computing device and comprising:
   a) identifying, according to said at least one MRI image, a plurality of brain image regions each of which contains a respective portion of diffusion index values of at least one diffusion index, which results from image processing performed on said at least one MRI image;
   b) for each of the brain image regions, calculating characteristic parameters based on the respective portion of the diffusion index values of said at least one diffusion index;
   c) forming a feature matrix using selected ones of the characteristic parameters of each of the brain image regions, the dimension of the feature matrix being the number of the selected ones of the characteristic parameters by the number of the brain image regions; and
   d) diagnosing the brain examined with one of predetermined categories of the neurological disorder by performing classification on the feature matrix via a classifier associated with the predetermined categories of the neurological disorder so that the neurological disorder in the brain examined is able to be diagnosed without the requirement of selecting a volume of interest (VOI) in said at least one MRI image or performing voxel-wise analysis on said at least one MRI image,
   subsequent to step a) and prior to step b), the method further comprising:
   e) performing a statistical transformation on the diffusion index values of said at least one diffusion index to result in transformed index values;
   f) for each of the brain image regions and prior to step d), determining based on a statistical test, whether the brain image region is discriminative for the categories of the neurological disorder;
   wherein step b) includes, for each of the brain image regions, calculating the characteristic parameters based on a portion of the transformed index values corresponding to the brain image region;
   wherein step d) includes performing classification via the classifier on the feature matrix that contains a combination of the characteristic parameters of the brain image regions which are determined to be discriminative for the categories of the neurological disorder;
   wherein step e) includes performing the statistical transformation over the whole of the diffusion index values of all of the brain image regions to result in the transformed index values so that distribution of the transformed index values of all of the brain regions approaches a normal distribution;
   wherein in step e), the statistical transformation is implemented by a Box-Cox transformation; and
   wherein the predetermined categories of neurological disorder include Parkinson's disease (PD), Alzheimer's disease (AD), and cerebral palsy (CP).

2. The method as claimed in claim 1, wherein in step b), for each of the brain image regions, the characteristic parameters includes a statistical value of the respective portion of the diffusion index values of said at least one diffusion index.

3. The method as claimed in claim 2, wherein in step b), the statistical value is one of a percentile and a mean.

4. The method as claimed in claim 3, wherein in step b), the percentile is one of a $10^{th}$ percentile, a $50^{th}$ percentile, a $90^{th}$ percentile.

5. The method as claimed in claim 1, wherein in step b), for each of the brain image regions, the characteristic parameters includes a statistical value of the portion of the transformed index values corresponding to the brain image region.

6. The method as claimed in claim 1, wherein in step a), the image processing performed on said at least one MRI image to result in said at least one diffusion index is one of diffusion tensor imaging (DTI), diffusion kurtosis imaging (DKI), neurite orientation dispersion and density imaging (NODDI), and the AxCaliber technique.

7. The method as claimed in claim 6, wherein in step a), said at least one diffusion index that results from DTI is one of fractional anisotropy (FA), mean diffusivity (MD), radial diffusivity (RD) and axial diffusivity (AXD), said at least one diffusion index that results from DKI is one of kurtosis fractional anisotropy (KFA), mean kurtosis (MK), radial kurtosis (KR) and axial kurtosis (KA), said at least one diffusion index that results from NODDI is one of intracellular volume fraction (Ficvf), cerebrospinal fluid volume fraction (Fiso), fitting objective function values (Fmin), concentration parameter of Watson distribution (Fkappa) and orientation dispersion index (ODI), and said at least one diffusion index that results from the AxCaliber technique is one of signal decay of the hindered diffusion fraction of water molecules (Eh) and signal decay of the restricted diffusion fraction of water molecules (Er).

8. The method as claimed in claim 1, wherein step a) includes identifying, according to a plurality of diffusion MRI images, a brain parcellation template and an anatomical image, the brain image regions.

9. A method for diagnosing a neurological disorder based on at least one magnetic resonance imaging (MRI) image that is associated with a brain examined, said method to be implemented by a computing device and comprising:
   a) identifying, according to said at least one MRI image, a plurality of brain image regions each of which contains a respective portion of diffusion index values of at least one diffusion index, which results from image processing performed on said at least one MRI image;
   b) for each of the brain image regions, calculating at least one characteristic parameter based on the respective portion of the diffusion index values of said at least one diffusion index;
   c) diagnosing the brain examined with one of predetermined categories of the neurological disorder by performing classification on a combination of the characteristic parameters of the brain image regions via a classifier associated with the predetermined categories of the neurological disorder so that the neurological disorder in the brain examined is able to be diagnosed without the requirement of selecting a volume of interest (VOI) in said at least one MRI image or performing voxel-wise analysis on said at least one MRI image,
   subsequent to step a) and prior to step b), the method further comprising:
   d) performing a statistical transformation on the diffusion index values of said at least one diffusion index to result in transformed index values;

subsequent to step c), the method further comprising:
e) validating correctness of classification using a leave-one-out cross validation,
wherein step b) includes, for each of the brain image regions, calculating said at least one characteristic parameter based on a portion of the transformed index values corresponding to the brain image region; and
prior to step c), the method further comprising f) for each of the brain image regions, determining based on a statistical test, whether the brain image region is discriminative for the categories of the neurological disorder;
wherein step d) includes, for each of the brain image regions, performing the statistical transformation over the portion of the diffusion index values corresponding to the brain image region to result in the transformed index values so that distribution of the transformed index values corresponding to the brain image region approaches a normal distribution; and
wherein the predetermined categories of neurological disorder include Parkinson's disease (PD), Alzheimer's disease (AD) and cerebral palsy (CP).

\* \* \* \* \*